(12) United States Patent
Uneyama et al.

(10) Patent No.: US 6,380,415 B2
(45) Date of Patent: Apr. 30, 2002

(54) PROCESS FOR PRODUCING OCTAFLUORO [2,2]PARACYCLOPHANE

(75) Inventors: Kenji Uneyama; Hideki Amii, both of Okayama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/781,961

(22) Filed: Feb. 14, 2001

(30) Foreign Application Priority Data

Feb. 14, 2000 (JP) .......................................... 12-035548

(51) Int. Cl.$^7$ .................................................. C02F 7/08
(52) U.S. Cl. ...................... 556/478; 556/480; 570/129
(58) Field of Search .......................... 570/129; 556/480, 556/478

(56) References Cited

U.S. PATENT DOCUMENTS

| | | | | |
|---|---|---|---|---|
| 5,210,341 A | * | 5/1993 | Dolbier et al. ........... | 570/129 X |
| 5,286,862 A | * | 2/1994 | Schubert et al. ......... | 556/480 X |
| 5,486,638 A | * | 1/1996 | Klipa et al. .................. | 556/480 |
| 6,156,918 A | * | 12/2000 | Winterfeld .................. | 556/480 |
| 6,194,620 B1 | * | 2/2001 | Maruyama .............. | 570/129 X |

FOREIGN PATENT DOCUMENTS

| | | |
|---|---|---|
| FR | 2109416 | 4/1975 |
| RU | 2032654 | 4/1995 |
| WO | 9824743 | 6/1998 |

OTHER PUBLICATIONS

W.R. Hasek, "The Chemistry of Sulfur Tetrafluoride. II. The Fluorination of Organic Carbonl Compounds" Organic and Biological Chemistry, 1960.

Casreact Database, Article No. 124:116848, 2001.

S. W. Chow, "The Synthesis of 1,1,2,2,9,9,10,10–Octafluoro [2.2] paracyclophane The Journal of Organic Chemistry "1970.

W. Dolbier, "A New and Practical Synthesis of Octafluoro [2.2]paracyclophane" J. Org. Chemistry, 1997.

A. Roche, "Electrophilic Substitution of 1,1,2,2,9,9,10, 10–Octafluoro [2.2]paracyclophane" J. Org. Chemistry, 1999.

M. Kako, "Photoinduced Novel Silylation of $CF_3$–substituted Benzenes with Disilane and Trisilane" Chemistry Community, 1993.

* cited by examiner

*Primary Examiner*—Paul F. Shaver
(74) *Attorney, Agent, or Firm*—Crowell & Moring LLP

(57) ABSTRACT

A process for producing an octafluoro[2,2]paracyclophane includes the steps of (a) reacting 1,4-bis(trifluoromethyl) benzene with a halogenated silane represented by the general formula (1), in the presence of a low valence metal, thereby obtaining a novel compound (precursor) represented by the general formula (2); and (b) conducting in the presence of a fluoride ion a dimerization of the compound into the octafluoro[2,2]paracyclophane, $$R_3SiX \quad (1)$$

where each R is independently an alkyl group or aryl group, and X is a halogen atom,

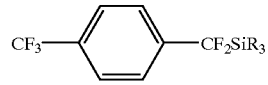

(2)

where R is defined as above. It is possible to produce octafluoro[2,2]paracyclophane with a high yield from 1,4-bis(trifluoromethyl)benzene, which is easily available, via the above compound.

23 Claims, No Drawings

PROCESS FOR PRODUCING OCTAFLUORO [2,2]PARACYCLOPHANE

BACKGROUND OF THE INVENTION

The present invention relates to a process for producing octafluoro[2,2]paracyclophane, which is useful as an intermediate for functional materials. This compound is particularly useful as a raw material for a heat-resistant parylene polymer film.

There are several processes for producing octafluoro[2,2]paracyclophane. J. Org. Chem. 1970, 35, 20–22 discloses a process for producing this target compound with a yield of 9–28% by a pyrolytic dimerization of a compound represented by the general formula (1) at a temperature of 600–800° C.,

(1)

where X is chlorine, bromine or $SO_2R'$ where R' is an alkyl group. U.S. Pat. No. 5,210,341 discloses a process for producing the target compound with a yield of 32% by a reductive dimerization of the compound represented by the general formula (1) where X is bromine, by $TiCl_4$—$LiAlH_4$ at 70° C. There is another process for producing the target compound by a reductive dimerization of the compound represented by the general formula (1) wherein X is bromine, by a combination of $Bu_3SnSiMe_3$ and CsF (see J. Org. Chem., 1997, 62, 7500–7502 and J. Org. Chem., 1999, 64, 9137–9143).

WO 98/24743 discloses a process for producing 1,4bis(difluoromethyl)benzene by the steps of (a) chlorinating paraxylene to obtain 1,4-bis(dichloromethyl)benzene and (b) fluorinating this compound by a metal fluoride into the target product. In this publication, it is proposed that 1,4-bis(dichloromethiyl)benzene is fluorinated with CsF or KF under a slurry condition at a temperature of 180° C. or higher.

Chemical Abstract, Vol. 124, 116848 discloses a process for producing 1,4-bis(trifluoroemthyl)benzene by fluorinating 1,4-bis(dibromomethyl)benzene by antimony trifluoride in the absence of solvent under a condition of 100–150° C. and 20–100 mmHg.

J. Am. Chem., Soc., 82, 543 (1960) discloses a fluorination of terephthalaldehyde by sulfur tetrafluoride at 150° C. French Patent 2109416 discloses a fluorination of terephthalaldehyde by molybdenum fluoride and boron trifluoride.

It is disclosed in J. Chem. Soc., Chem. Commun., 1993, 678 that 1-trifluoromethyl-4-difluorotrimethylsilylmethylbenzene can be synthesized by a silylmethylation of bis(trifluoromethyl)benzene through a photo-inducing reaction using tetramethyldisilane.

SUMMARY OF THE INVENTION

It is an object of the present invention to provide a process for producing octafluoro[2,2]paracyclophane with a high yield, using La raw material that is easily available.

According to the present invention, there is provided a process for producing octafluoro[2,2]paracyclophane. This process comprises:

reacting 1,4-bis(trifluoromethyl)benzene with a halogenated silane represented by the general formula (1), in the presence of a low valence metal, thereby obtaining a compound represented by the general formula (2); and conducting in the presence of a fluoride ion a dimerization of said compound into said octafluoro [2, 2]p aracyclophane, $$R_3SiX \qquad (1)$$

where each R is independently an alkyl group or aryl group, and X is a halogen atom,

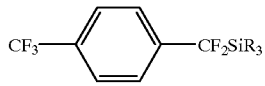
(2)

where R is defined as above.

DESCRIPTION OF THE PREFERRED EMBODIMENTS

The inventors have eager examined a dimerization of 1,4-bis(trifluoromethyl)benzene by removing fluorine atom from this compound. In this examination, we unexpectedly found that it is possible to easily break C-F bond, which is generally difficult to be broken due to its large bonding energy, of 1,4-bis(trifluoromethyl)benzene by setting a special intermediate (as a precursor of octafluoro[2,2] paracyclophane), that is, the compound represented by the general formula (2), and that it is possible to produce octafluoro[2,2]paracyclophane by a dimerization of this compound.

Hereinafter, the reaction of 1,4-bis(trifluoromethyl) benzene with the halogenated silane may be referred to as the first step, and the dimerization may be referred to as the second step.

The halogenated silane used in the first step is not particularly limited. In the general formula (1) representing the halogenated silane, the alkyl group (R) may be a lower alkyl group (e.g., methyl group, ethyl group, propyi group, or isopropyl group), and the aryl group (R) may be phenyl group or tolyl group. Furthermore, X may be chlorine, bromine or. iodine. Preferable examples of the halogenated silane are chlorotrimethylsilane, chlorotriethylsilane, chlorophenyldimethylsilane, chlorodiphenylmethylsilane, and bromotriethylsilane. Of these, chlorotrimethylsilane is the most preferable, since it is easily available.

The amount of the halogenated silane to be used in the first step may be 1 mole or greater (from the viewpoint of stoichiometry), preferably about 1–50 moles, more preferably about 1–10 moles, per mole of 1,4-bis(trifluoromethyl) benzene.

It is optional to use a solvent in the first step, as long as the solvent is inert under reaction conditions of the first step. Examples of such solvent are aliphatic hydrocarbons (e.g., pentane, hexane and heptane), aromatic hydrocarbons (e.g., benzene, toluene and xylene), nitrites (e.g., acetonitrile, propionitrile, phenylacetonitrile, isobutyronitrile, and benzonitrile), acid amides (e.g., N,N-dimethylformamide, N,N-dimethylacetoamide, methylformamide, formamide, hexamethylphosphoric acid, and hexamethyl phosphoric acid triamide), and lower ethers (e.g., tetrahydrofuran, 1,2-dimethoxyethane, diglyme, triglyme, diethyl ether, 1,2-epoxyethane, 1,4-dioxane, dibutyl ether, t-butyl methyl ether, and substituted tetrahydrofuran). Of these, N,N-dimethylformamide and tetrahydrofuran are preferable. It is optional to use a mixture of at least two of these solvents. The solvent may be in an amount of about 1–100 parts by weight, preferably 1–20 parts by weight, per one part by weight of the 1,4-bis(trifluoromethyl)benzene.

It is preferable to remove water as much as possible from the solvent to be used in the first and second steps. It is, however, not necessary to remove water completely. The amount of water generally contained in a commercially available solvent is acceptable in the first and second steps. Therefore, it is possible to directly use a commercially available solvent in the invention, without removing water.

The low valence metal used in the first step is not particularly limited. In this specification, the low valence metal can be defined as being an element that belongs to typical elements and as being a metal that does not have an oxidation number of 5 or greater under a normal condition. It may be a metal element, for example, selected from magnesium, zinc, copper, iron, cadmium, tin, titanium, and sodium. Furthermore, the low valence metal may be in the form of a metal alloy containing at least one of these metal elements as a major component. Examples of such metal alloy ate an alloy of zinc and copper, Raney nickel, an alloy of silver and zinc, and an alloy of copper and magnesium. Furthermore, metal ion in a low oxidation state may also be applicable, such as titanium trichloride, samarium diiodide, and chromium dichloride. Furthermore, such metal ion in a low oxidation state may be in the form of a metal complex such as sodium naphthalenide, sodium benzophenon ketyl complex, or tetrakis(triphenylphosphine)palladium. Still furthermore, the low valence metal may be in the form of a mixture of the metal element or the metal alloy and the metal compound or the metal complex. Examples of such mixture are a mixture of titanium tetrachloride and metallic zinc, a mixture of titanocene dichloride and zinc, a mixture of samarium diiodide and samarium, and a mixture of samarium diiodide and magnesium. Of these, it is preferable to use magnesium or a mixture containing magnesium.

When the low valence metal is used in the form of a metal element (metallic form), its shape is not particularly limited. In fact, it may be in the form of powder, granules, aggregates, porous solid, chips or rod. For example, it is possible to directly use a magnesium having a known shape generally used for Grignard reaction. The amount of the low valence metal may be about 1–50 moles, preferably about 1–10 moles, per mole of the 1,4-bis(trifluoromethyl) benzene.

The reaction temperature of the first step may be a temperature of −78 to 120° C. The reaction time may be varied depending on the reagents, and may be adjusted to about 10 minutes to about 20 hours. The reaction pressure of the first step may be in the vicinity of normal pressure. The other reaction conditions of the first step may be the same as those of a reaction using a conventional organic magnesium compound.

In the first step, it is optional to use various reaction accelerations generally used in Grignard reaction, in order to accelerate the reaction. For example, it is optional to add to the reaction system a halogen (e.g., bromine or iodine), Grignard's reagent, an organic halide (e.g., ethyl bromide, methyl iodide, methylene diiodide, ethyl iodide, or β-bromoethyl ether), or ethyl orthosilicate. Furthermore, it is optional to conduct stirring or ultrasonic agitation as the reaction acceleration.

Each reaction of the first and second steps does not depend on pressure. Thus, when the reaction is conducted under a pressurized condition, the pressure may be 1.0 MPa or lower. The reaction may be conducted under an atmosphere of air. It is, however, preferable to conduct the reaction under an atmosphere of inert gas (e.g., nitrogen, argon or helium).

It is preferable to subject a crude product of the first step, which contains the target compound represented by the general formula (2), to purification, depending on the use of this target compound. This purification is not particularly limited, and may be conducted by a conventional extraction or column chromatography.

As stated above, the second step is conducted by a dimerization of the compound (represented by the general formula (2)) into octafluoro[2,2]paracyclophane, in the presence of a fluoride ion. This presence of a fluoride ion can be achieved by adding a fluoride. This addition of fluoride may be replaced with the addition of a compound that accelerates the release of fluorine atom from the compound represented by the general formula (2). Examples of the fluoride are alkali metal fluorides (e.g., sodium fluoride, potassium fluoride, and cesium fluoride), alkali earth metal fluorides (e.g., barium fluoride and magnesium fluoride ), fluorides of other metals (e.g., copper fluoride and chromium fluoride), and ammonium fluoride. Examples of the fluorine-release-accelerating compound are quaternary ammonium salts in which an alkyl or aryl group is bonded to N, such as triethylbenzylammonium chloride, tetramethylammonium chloride, triethylbenzylammonium bromide, trioctylmethylammonium chloride, tributylbenzylammonium chloride, trimethylbenzylammonium chloride, N-laurylpyridinium chloride, n-butylammonium hydroxide, tetramethylammonium hydroxide, trimethyjbenzylammonium hydroxide, trimethylphenylammonium bromide, tetramethylammonium bromide, tetraethylammonium bromide, tetra-n-butylammonium bromide, tetrabutylammonium hydrosulfate, N-benzylpicolinium chloride, tetramethylammonium iodide, and tetra-n-butylammonium iodide. The anion of the fluorine-release-accelerating compound is not particularly limited. The amount of the fluoride or the fluorine-release-accelerating compound may be a catalytic amount. In fact, it may be 0.0001. to 1 mole, preferably 0.001 to 0.5 moles, per mole of the 1,4-bis(trifluoromethyl) benzene. Furthermore, it is optional to use a crown ether in order to accelerate the second step. The amount of this crown ether may be about 0.001 to 10 moles, preferably 0.01 to 1 mole, per mole of the fluoride.

It is preferable to use a solvent in the second step. This solvent is preferably a nonpolar solvent or a solvent that is low in polarity. In fact, Examples of the solvent are aromatic hydrocarbons, condensed-ring aromatic compounds, polycyclic aromatic compounds, and aliphatic hydrocarbons. Of these solvents, aromatic hydrocarbons are preferable. Concrete examples of the aromatic hydrocarbons are toluene, xylene, ethylbenzene, cumene, mesitylene, durene, and tetralin). Of these, mesitylene, o-xylene, m-xylene, and p-xylene are particularly preferable. It is optional to use a mixture of aromatic hydrocarbons (e.g., SOLVES SO (trade name)). Examples of the condensed-ring aromatic compounds and polycyclic aromatic compounds are mono-, di- and tri-methylnaphthalenes, mono-, di- and tri-isopropylnaphthalene, ethyl diphenyl, and dibenzyltoluene. Examples of the aliphatic hydrocarbons are heptane and octane. It is optional to use a mixture of at least two of the above-mentioned solvents. When the second step is conducted under a normal pressure, it is preferable to use a solvent having a high boiling point. So that, these exemplary solvents are preferably those having a boiling point of higher than 100° C. more preferably 120–300° C. It is, however, possible to use a lower-boiling-point solvent in the reaction under a pressurized condition.

The reaction temperature of the second step may be about 100–300° C., preferably about 130–250° C. If it is lower than about 100° C., desilylated compounds, for example, a compound represented by the following formula may be produced. With this, the yield of octafluoro[2,2] paracyclophane may be lowered.

The second step can be conducted by charging a reaction vessel with 1-trifluoromethyl-4-cdifluorotrimethylsilylmethylbenzene, a solvent, a fluoride and the like and then by maintaining the reaction vessel at a predetermined temperature for a predetermined time. During the reaction, it is optional to conduct stirring and reflux of the contents of the reaction vessel. After the reaction, a solid matter can be collected by removing the catalyst and then by distilling the solvent off or by filtration. This solid matter can be purified by a conventional method. For example, it may be recrystallization, sublimation or column chromatography.

The following nonlimitative examples are illustrative of the present invention.

EXAMPLE 1

At first, 288 mg (12 mmol) of magnesium powder and 2.6 g (24 mmol) of chlorotrimethylsilane were added to 20 ml of N,N-dimethylformamide (DMF). Then, 1.28 g (6 mmol) of 1,4-bis(trifluoromethyl)benzene were dropped to the resulting mixture, followed by stirring for 30 minutes under an argon atmosphere at room temperature. Then, ammonium chloride was added, thereby terminating the reaction. Then, the reaction liquid was extracted with hexane, and the resulting extract (hexane solution) was dried with magnesium sulfate. Then, it was found by $_{19}$FNMR for analyzing fluorine that the dried extract contained 64% of 1-trifluoromethyl-4-difluorotrimethylsilylmethylbenzene and 5% of 1-trifluoromethyl-4-fluorotrimethylsilylmethylbenzene. The dried extract was subjected to a Kugelrohr distillation, thereby obtaining 961 mg of 1-trifluoromethyl-4-difluorotrimethylsilylmethylbenzene (yield: 56%) in the form of a colorless oil-like substance.

The analytical data of this product are as follows. Boiling point: 95° C. (30 mmHg); $^1$HNMR (200 MHz, CDCl$_3$): δ=0.15 (S, 9H), 7.46 (d, J=8.6Hz, 2H), 7.68 (d, J=8.6Hz, 2H); $^{19}$FNMR (188 MHz, CDCl$_3$, internal standard: C$_6$F$_6$): δ=48.7(s, 2F), 99.0 (s, 3F); Elemental analysis (C$_{10}$H$_{13}$F$_3$Si): calculated value (C: 79.27, H: 9.15); measured value (C: 79.53, H: 9.14).

EXAMPLES 2 AND 3

In each of these examples, Example 1 was repeated except that the reaction conditions were modified as shown in Table 1.

TABLE 1

|  | a* (mmol) | Mg (mmol) | Reaction Temp. (° C.) | Reaction Time (hr) | Product Yield (%) | |
|---|---|---|---|---|---|---|
|  |  |  |  |  | b* | c* |
| Ex. 1 | 6.0 | 12.0 | Room Temp. | 0.5 | 64 | 5 |
| Ex. 2 | 0.6 | 0.66 | Room Temp. | 3 | 35 | 7 |
| Ex. 3 | 0.6 | 1.20 | Room Temp. | 1 | 58 | 15 |

*a: 1,4-bis(trifluoromethyl)benzene;
*b: 1-trifluoromethyl-4-difluorotrimethylsilylmethylbenzene;
*c: 1-trifluoromethyl-4-fluorotrimethylsilylmethylbenzene, as shown by the following formulas.

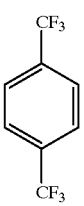

(a)

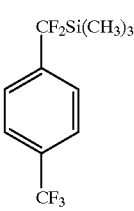

(b)

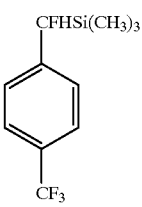

(c)

EXAMPLE 4

At first, 107 mg (0.4 mmol) of 1-trifluoromethyl-4-difluorotrimethylsilylmethylbenzeene and 6.1 mg (0.04 mmol) of cesium fluoride were added to 1.0 ml of mesitylene. Then, the reaction was conducted for 24 hr for 160° C. After the reaction, the reaction liquid was analyzed by $^{19}$FNMR for fluorine. With this, the yield of octafluor[2,2]paracyclophane was found to be 53%. The reaction liquid was filtered, followed by recrystallization from chloroform at room temperature, thereby obtaining 30 mg of a colorless octafluoro[2,2]paracyclophane (yield: 48%).

The analytical data of this target product were as follows.

Melting point: 261° C.; $^1$HNMR (200 MHz, CDCl$_3$)): δ=7.16 (s, 8H); $^{19}$FNMR (188 MHz, CDCl$_3$, internal standard: C$_3$F$_6$): δ=43.5(s, 8F).

EXAMPLE 5 AND REFERENTIAL EXAMPLE

In each of Example 5 and Referential Example, Example 4 was repeated except that the reaction conditions were modified as shown in Table 2. In Referential Example, 1-trifluoromethyl-4-difluoromethylbenzene was formed.

TABLE 2

| | b* (mmol) | Solvent | Reaction Temp. (° C.) | Reaction Time (hr) | Product Yield (%) d* |
|---|---|---|---|---|---|
| Ex. 4 | 0.4 | mesitylene | 160 | 24 | 53 |
| Ex. 5 | 0.4 | o-xylene | 140 | 24 | 21 |
| Ref. Ex. | 0.4 | toluene | 100 | 24 | a trace amount |

*b: 1-trifluoromethyl-4-difluorotrimethylsilylmethylbenzene; and
*d: octafluoro[2,2]paracyclophane, as shown in the following formulas.

(b)

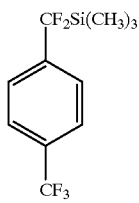

(d)

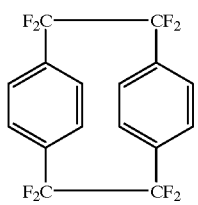

The entire disclosure of Japanese Patent Application No. 2000-35548 filed on Feb. 14, 2000, including specification, claims and summary, is incorporated herein by reference in its entirety.

What is claimed is:

1. A process for producing octafluoro[2,2]paracyclophane, comprising:

reacting 1,4-bis(trifluoromethyl)benzene with a halogenated silane corresponding to formula (1):

$$R_3SiX \quad (1)$$

wherein each R is independently an alkyl group or an aryl group, and

X is a halogen atom in the presence of a low valence metal, thereby obtaining a compound corresponding to formula (2):

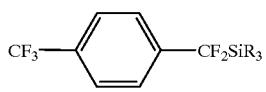  (2)

wherein R is defined as above, and dimerizing said compound corresponding to formula (2) in the presence of fluoride ion to form the octafluoro[2,2]paracyclophane.

2. A process for producing a compound represented by the general formula (2), comprising:

reacting 1,4-bis(trifluoromethyl)benzene with a halogenated silane represented by the general formula (1), in the presence of catalyst comprising a low valence metal, thereby obtaining said compound,

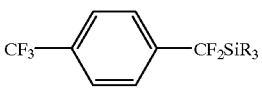  (2)

where each R is independently an alkyl group or aryl group, $R_3SiX$ (1) where R is defined as above, and X is a halogen atom.

3. A process for producing octafluoro[2,2]paracyclophane, comprising:

conducting in the presence of a fluoride ion a dimerization of a compound, which is represented by the general formula (2) into said octafluorof[2,2]paracyclophane,

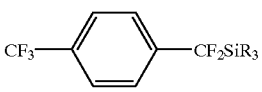  (2)

where each R is independently an alkyl group or aryl group.

4. A process according to claim 1, wherein said halogenated silane is selected from the group consisting of chlorotrimethylsilane, chlorotriethylsilane, chlorophenyldimethylsilane, chlorodiphenylmethylsilane, and bromotriethylsilane.

5. A process according to claim 4, wherein said halogenated silane is chlorotrimethylsilane.

6. A process according to claim 1, wherein said halogenated silane is in an amount of 1 mole or greater per mole of said 1,4-bis(trifluoromethyl)benzene.

7. A process according to claim 1, wherein said reacting is conducted in a solvent.

8. A process according to claim 7, wherein said solvent is in an amount of 1–100 parts by weight per one part by weight of said 1,4-bis(trifluoromethyl)benzene.

9. A process according to claim 1, wherein said low valence metal comprises a metal element selected from the group consisting of magnesium, zinc, copper, iron, cadmium, tin, titanium, and sodium.

10. A process according to claim 9, wherein said low valence metal is magnesium.

11. A process according to claim 1, wherein said low valence metal is in the form of a metal alloy.

12. A process according to claim 1, wherein said low valence metal is in the form of a metal compound.

13. A process according to claim 1, wherein said low valence metal is in the form of a metal complex.

14. A process according to claim 1, wherein said low valence metal is in an amount of 1–50 moles per mole of said 1,4-bis(trifluoromethyl)benzene.

15. A process according to claim 1, wherein said reacting is conducted at a temperature of from −78 to 120° C.

16. A process according to claim 1, wherein said dimerizing is conducted in the presence of an alkali metal fluoride comprising said fluoride ion.

17. A process according to claim 16, wherein said alkali metal fluoride is cesium fluoride.

18. A process according to claim 1, wherein said dimerizing is conducted in a solvent selected from the group consisting of aromatic hydrocarbons, condensed-ring aromatic compounds, polycyclic aromatic compounds, and aliphatic hydrocarbons.

19. A process according to claim 18, wherein said solvent is an aromatic hydrocarbon.

20. A process according to claim 18, wherein said solvent has a boiling point of 120–300° C.

21. A process according to claim 19, wherein said solvent has a boiling point of 120–300° C.

22. A process according to claim 19, wherein said solvent is selected from the group consisting of mesitylene, o-xylene, m-xylene and p-xylene.

23. A process according to claim 1, wherein said dimerizing is conducted at a temperature of from 100 to 300° C.

* * * * *